(12) United States Patent
Maschke

(10) Patent No.: US 7,384,376 B2
(45) Date of Patent: Jun. 10, 2008

(54) APPARATUS AND METHOD FOR TRAINING ADJUSTMENT IN SPORTS, IN PARTICULAR IN RUNNING SPORTS

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 554 days.

(21) Appl. No.: 10/856,386

(22) Filed: May 28, 2004

(65) Prior Publication Data

US 2005/0164832 A1 Jul. 28, 2005

(30) Foreign Application Priority Data

May 30, 2003 (DE) ............... 103 24 904

(51) Int. Cl.
*A63B 22/02* (2006.01)
*A63B 71/00* (2006.01)

(52) U.S. Cl. ............... 482/8; 482/51; 482/54; 600/411

(58) Field of Classification Search ............ 482/1–9, 482/51, 54, 900–902; 600/300, 301, 368, 600/411, 513, 520; 601/23–26; 434/247
See application file for complete search history.

(56) References Cited

U.S. PATENT DOCUMENTS

| 4,622,980 | A | | 11/1986 | Kunig | |
| 5,081,991 | A | * | 1/1992 | Chance | 600/411 |
| 5,738,612 | A | | 4/1998 | Tsuda | |
| 6,411,841 | B2 | * | 6/2002 | Heikkila | 600/513 |
| 6,687,535 | B2 | * | 2/2004 | Hautala et al. | 600/520 |
| 6,736,759 | B1 | * | 5/2004 | Stubbs et al. | 482/8 |

FOREIGN PATENT DOCUMENTS

| DE | 41 02 031 C2 | 7/1992 |
| DE | 196 51 520 A1 | 6/1998 |
| DE | 199 09 852 | 9/2000 |
| DE | 199 09 852 A1 | 9/2000 |
| DE | 100 63 841 A1 | 6/2002 |
| WO | WO 99/55431 | 11/1999 |
| WO | WO 00/53091 | 9/2000 |

\* cited by examiner

*Primary Examiner*—Glenn Richman
(74) *Attorney, Agent, or Firm*—Schiff Hardin LLP

(57) ABSTRACT

For training adjustment in sports, particularly running sports, an apparatus and appertaining method are provided with which a simple, non-invasive and automatic determination of the lactate balance point is possible. The apparatus comprises a motorized treadmill for which a running speed can be predetermined by a control unit, whereby the control unit is connected to a pulse measurement device to supply a measurement value of the heart rate of a test person, and whereby the control unit comprises a module to determine the lactate balance point, this module being fashioned to successively increase the running speed in the training course, to register the time curve of the heart rate, and to determine the lactate balance point of the test person via evaluation of the dependency of the heart rate on the running speed.

11 Claims, 3 Drawing Sheets

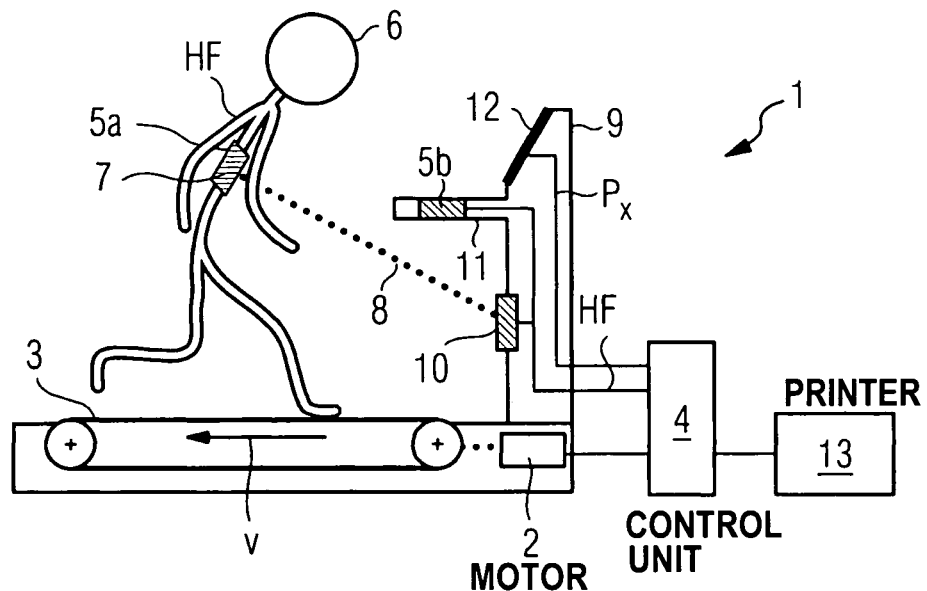
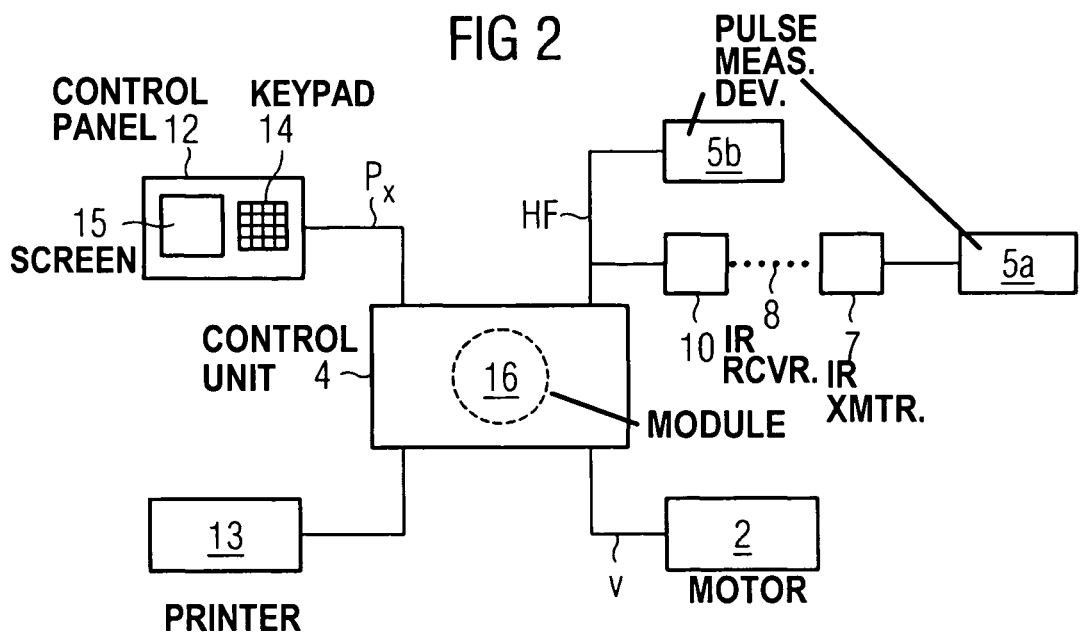

FIG 3
FIG 3a
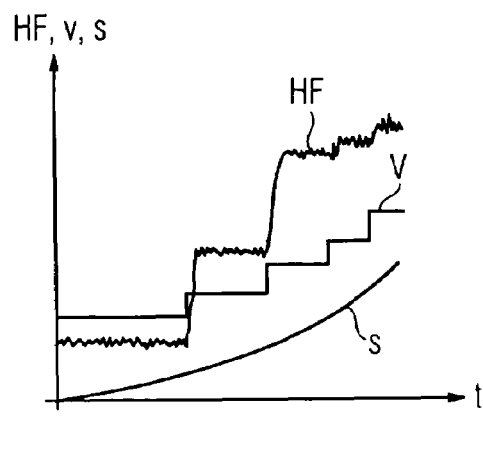
FIG 3b
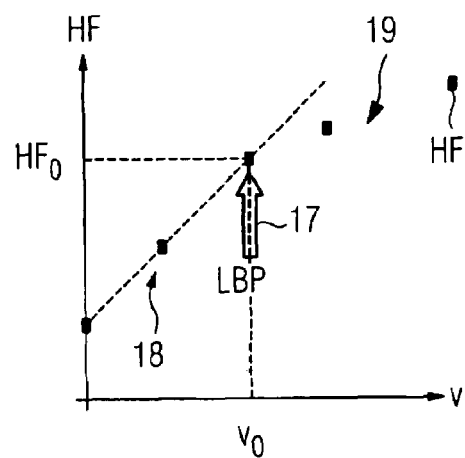
FIG 4
FIG 4a
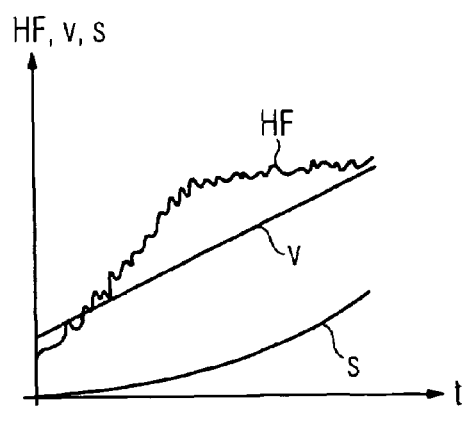
FIG 4b
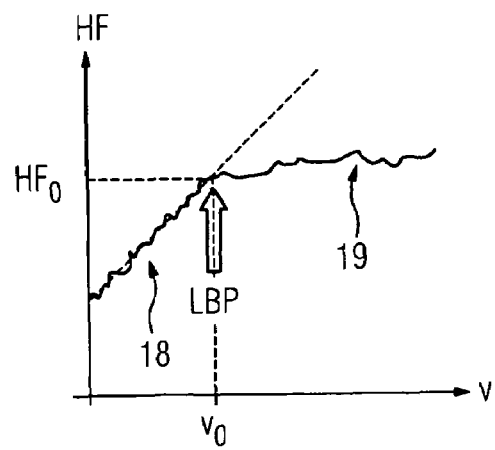

Name: Maier, Josef

Born: 15 May 1970

Runner experience: 2 years, i.e advanced runner

Low-risk:
    * non-smoker  $P_x$
    * no high blood pressure
    * no heart disease
    * the last medical exam was one year ago Lactate Balance Point (LBP): 140 Beats/minute at 9 km/h Included measurement
curve  ---------------------

Training recommendation:

Perform 70% of the training below the LBP and 30% of the training above the LBP. Divide training into 3 units per week with at least one day training break between the units.

Training plan (weekly):

Unit 1: 1 hour with heart rate range 125-135 beats per minute.
One day break
Unit 2: 1 hour with heart rate 130-140 beats per minute.

APPARATUS AND METHOD FOR TRAINING ADJUSTMENT IN SPORTS, IN PARTICULAR IN RUNNING SPORTS

BACKGROUND OF THE INVENTION

The invention concerns an apparatus and method for training adjustment in sports, particularly running sports.

To generate muscle power/performance, a human or other muscle requires oxygen that must be supplied by the organism. The greater the power, the greater the need for oxygen as well. At a certain power limit, the body will go into what is known as "oxygen debt". This means that the blood contains too small an oxygen ratio to be able to supply the oxygen necessary to generate power. The metabolism in the muscle then passes into the anaerobic range marked by oxygen deficiency. In contrast to this, the metabolism given sufficient oxygen supply is designated as aerobic.

Complete burning of the energy carrier glucose drawn on by the body does not ensue in the muscle in the anaerobic range. As a result of this, "combustion shortfalls" accumulate in the body that can no longer completely metabolized as a result of the oxygen deficiency. The muscle thus stressed is "acidic" and requires a longer time in order to regenerate after the stress.

In sport types that are connected with high body stress, particularly running sports, it is therefore important that the training is implemented predominantly in the aerobic range, and only a small portion in the anaerobic range. For a non-professional athlete, for example, the aerobic training phase should amount to approximately 80% of the overall training.

For training adjustment, it is typical in sports medicine to determine what is known as the lactate balance point (LBP). Lactate (lactic acid) is a decomposition product of glucose that—as specified in the preceding—is created when the oxygen in the organism is no longer sufficient for combustion. In the anaerobic range, lactate therefore accumulates in the body, while in the aerobic range, excess lactate is metabolized again. At the threshold between aerobic metabolism and anaerobic metabolism, the lactate level in the organism remains in balance. This defines the LBP. If the LBP and the associated heart rate of an athlete are known, the athlete can optimize his training according to this.

The lactate value is conventionally determined with a lactate measurement device which effects a blood analysis of blood samples that are extracted from the athlete at different stresses. Physiological fundamentals and a method for lactate measurement are, for example, specified in German Patent Document DE 199 09 852 A1. The known solution is, disadvantageously, an invasive method, especially since blood samples must be extracted from the test person (e.g., an athlete) to be tested. This is, on the one hand, sometimes painful for the athlete. On the other hand, the blood extraction is always connected with a risk of infection, for example, with hepatitis or HIV, for both the test person and for the examiner. To reduce this infection risk, high hygiene standards are in turn necessary that make the method elaborate and expensive.

A conventional non-invasive method to determine the LBP, designated as a "Conconi test", is increasingly being used in sports medicine. In this method, a test person runs on a 400 m athletic track for a length of 200 m with a predetermined speed, for example 8 km/h. After respectively 200 m, the test person increases the tempo in stages, for example, by respectively 0.5 km/h. At each 200 m mark of the athletic track, the test person notes his current heart rate and calls it out to an attendant after respectively circling the athletic track. The test person runs on the track until he has reached a power limit, meaning he cannot further increase the speed.

For test evaluation, the heart rate is plotted against the associated running speed in a two-dimensional (X-Y) diagram. A characteristic finding hereby results: in the aerobic range, given a comparably low power, the heart rate runs nearly linearly with the running speed. This means that the heart rate increases in the same proportion as the power generated by the test person. This regularity is broken at the threshold to the anaerobic metabolism. In the anaerobic high-power range, the heart rate increases comparatively only slightly with further-increasing power or, respectively, running speed. The function of the heart rate dependent on the running speed thus shows a clear, more or less sharp break at the transition from the aerobic low-power range to the anaerobic high-power range, via which the LBP is determined. The heart rate characteristic for the LBP and the associated running speed can be simply read from the X/Y diagram.

However, the Conconi test is comparably elaborate and can hardly be executed without a trained attendant. Additionally, with the Conconi test the LBP can be determined only comparatively imprecisely, due to the weather dependency and the capability of the test person to precisely control his speed.

SUMMARY OF THE INVENTION

The invention is based on the object to provide an apparatus and appertaining method for training adjustment in sports, particularly running sports, with which a simple, non-invasive and automatic determination of the lactate balance point is possible.

This object is inventively achieved by an apparatus for training adjustment in sports, comprising: a motorized treadmill for which a running speed can be predetermined; a pulse measurement device configured to supply a measurement value of the heart rate of a test person; a control unit connected to the pulse measurement device, the control unit configured to control the running speed of the motorized treadmill, the control unit comprising: a module to determine a lactate balance point, the module comprising: a mechanism to successively increase the running speed in a training course; a mechanism to register a time curve of the heart rate; and a mechanism to determine the lactate balance point of the test person via evaluation of a dependency of the heart rate on the running speed.

This object is also achieved by a method for performing a training adjustment, comprising: measuring a heart rate of a test person; registering a time curve of the heart rate; controlling a running speed of a motorized treadmill by successively increasing the running speed in a training course; and determining a lactate balance point by evaluating a dependency of the heart rate on the running speed.

According to the invention, the apparatus comprises a motorized treadmill for a test person. Furthermore, a control unit is provided via which a running speed can be predetermined for the treadmill. The control unit is connected with a pulse measurement device to measure the heart rate of the test person. The control unit comprises a module to determine the lactate balance point (LBP) for which the heart rate of the test person can be supplied as an input value. This module is fashioned to successively increase the running speed of the treadmill in the training course, and at the same time to record the time curve of the heart rate of the test person. Furthermore, the module is fashioned to evaluation the functional dependency of the heart rate on the running speed, and from this to determine the LBP of the test person.

Various embodiments of the invention and advantages thereof are described below. An automatic, non-invasive determination of the LBP is advantageously possible with the specified apparatus. Medical knowledge or a trained attendant are therefore not necessary for implementation. The test person can thus use the apparatus for a self-test. The apparatus can be realized cheaply and comparably space-saving. This particularly allows the determination of the LBP within closed spaces such as a sports medicine practice, a fitness studio or any other closed training facility. Finally, the test result is available without time delay as a result of the automatic evaluation. In particular, no manual evaluation or post-processing of the test data is necessary. The test implementation thus requires only a comparably small temporal cost. This in particular also eases a frequent repetition of the test, as it is important for an optimized long-term adjustment of the training, particularly in competitive sports.

An advantage of the apparatus is in particular that, via control of the treadmill, the power to be generated by the test person in the form of the adjustable running speed can be predetermined exactly, whereby the LBP can be determined with high precision.

The module is appropriately fashioned to detect the transition heart rate at which the heart rate as a function of the running speed deviates from the linear low-power ratio in the aerobic range and transitions into the high-power ratio characteristic of the anaerobic range. The module determines this transition heart rate associated with the LBP via analysis of the heart rate curve with established mathematical methods of function analysis, for example differential formation, and/or via methods of linear or non-linear regression.

A variant of the inventive apparatus provides that the module increases the running speed in regular intervals, or alternatively increases the running time, similar to the conventional Conconi test. Here as well, the running speed is preferably increased in regular speed stages.

Moreover, however, the use of a motorized treadmill also allows possibilities that are not given or are barely given in the conventional Conconi test. Thus, it is provided in a particularly advantageous alternative embodiment that the module does not vary the running speed in stages, but rather as a continuous function increasing with the running time or a particular route. Such a continuous change of the running speed is, on the one hand, frequently felt to be more comfortable by the test person in comparison with a jumping speed change. On the other hand, a continual variation of the running speed also leads to an increase of the measurement precision in the determination of the LBP. The change of the running speed is understood as "continuous" when the running speed is, in fact, increased in stages; the speed stages are, however, so small (for example, 0.1 km/h or less) that the test person perceives the change of the running speed as quasi-continuous.

Optionally, in an embodiment, it is provided that a measurement value of the blood pressure of the test person is additionally supplied by a non-invasive blood pressure measurement device. The module displays the curve of the blood pressure and draws upon the dependency of the blood pressure on the running speed for support to determine the LBP.

The module is advantageously connected with the output unit. Alternatively or simultaneously, a monitor and/or a printer are provided as an output unit. Via the output unit, it is advantageously possible to output the measurement curve of the heart rate and/or the test result in image or text form. This preferably already ensues during the test course in order to given the test person a way at hand for self monitoring. In particular, given frequent repetition of the test, the test person can thus establish a coenesthesia (a body feeling or sense) for the arrival at the LBP by monitoring the test curve during the test course.

At least one test person-specific parameter can preferably be supplied to the module via an input apparatus. The age, weight, height, class (for example, beginner, amateur athlete, competitive athlete) and/or at least one health risk factor (for example, nicotine consumption, heart disorder, high blood pressure, etc.) are drawn upon as test person-specific parameters, particularly in an arbitrary combination. Based on these data, the module adjusts an individual test program using stored characteristic lines. The test person-specific parameter or parameters are in particular considered in the selection of the initial speed and the time curve of the running speed.

The module preferably compiles a training recommendation (that is output to the test person after the end of the test) using the determined LBP and the test person-specific parameter or parameters, with reference to stored characteristic lines.

DESCRIPTION OF THE DRAWINGS

Exemplary embodiments of the invention are subsequently explained in detail with reference to the following drawings.

FIG. 1 is a pictorial schematic representation of an apparatus for training adjustment in sports, particularly running sports, with a motorized treadmill and a control unit;

FIG. 2 is a schematic block circuit diagram of the control unit according to FIG. 1 and the peripheral devices connected with it;

FIGS. 3A, B are graphs showing an exemplary test course to determine the lactate balance point with running speed increased in stages, as well as the exemplary curve of the heart rate of a test person dependent on the running speed;

FIGS. 4A, B are graphs showing, in a representation according to FIGS. 3A, B, an alternative test curve in which the running speed is continuously increased; and FIG. 5 is an example of a training recommendation output by the apparatus according to FIG. 1.

DETAILED DESCRIPTION OF THE PREFERRED EMBODIMENTS

Referring to the Figures, in which parts and quantities corresponding to one another are always provided with the same reference characters, various embodiments of the invention are described below.

The apparatus 1 shown in FIG. 1 comprises a treadmill 3 driven by a motor 2. The motor 2 can be controlled by a control unit 4. The control unit 4 is particularly in the position to precisely set a predetermined treadmill speed (subsequently designated as a running speed v). The running speed v may be variable continuously or in stages in narrow speed steps of $\leq 0.1$ km/h.

The control unit 4 is furthermore connected with a pulse measurement device 5a. The pulse measurement device 5a is to be attached to the body of a test person 6 (i.e., an athlete to be tested), for example in the form of a chest belt. The pulse measurement device 5a communicates with the control unit 4, preferably via an infrared (IR) interface. For this, the pulse measurement device 5a comprises an IR transmitter 7 that is connected via a light line 8 with an IR receiver 10 arranged on a mount 9 of the treadmill 3. The IR receiver 10 is in turn connected with the control unit 4.

In the test course, the pulse measurement device 5a measures the heart rate HF of the test person 6 continuously or in short intervals. The measurement value of the heart rate HF is supplied to the control unit 4 as an input value via the IR interface formed from the IR transmitter 7 and the IR receiver 10.

Instead of the IR interface, any other type of wireless data transmission can also be used. Furthermore, the pulse measurement device 5a can also be connected with the control unit 4 via a conventional cable connection.

A further pulse measurement device 5a is additionally or alternatively integrated into a handhold 11 which is attached to the mount 9 of the treadmill 3.

In a similar (not explicitly shown) manner, the blood pressure of the test person 6 is optionally collected as an additional measurement quantity by way of a non-invasive blood pressure measurement device and supplied to the control unit 4.

Moreover, the apparatus 1 comprises a control panel 12 connected with the control unit 4. Data that are supplied to the control unit 4 as input values can by input by the test person 6 via this control panel 12. On the other hand, the control panel 12 also serves as an output unit of the control unit 4, in that output values are given to the control panel 12 by the latter and are displayed there for the test person 6 in visual or audio-visual form.

The control unit 4 is finally connected with a printer 13 as a further output device.

FIG. 2 shows the control unit 4 again in a schematic circuit block diagram, as well as the peripheral devices (for example, the motor 2, the pulse measurement devices 5a and 5b, the control panel 12 and the printer 13) connected with this. From this representation, it is clear that the control panel 12 is provided with input and output for data. A keypad 14 preferably serves as a data input. A screen 15 or alternatively a light-emitting diode display is provided as a data output.

The control unit 4 is provided with a module 16 to determine the lactate balance point (LBP). This module 16 is preferably a software module.

The apparatus 1 enables the training adjustment of the test person 6, in that it determines his LBP, automatically generates an individual training instruction, and outputs it to the test person 6. For this, the module 16 here controls a test program, in the course of which it successively increases the running speed v of the treadmill 3 and simultaneously records the curve of the heart rate HF of the test person 6.

Before the beginning of the test, the module 16 prompts the test person 6 (via the control panel 12) to input a plurality of test person-specific parameters $P_x$. These parameters $P_x$ comprise the age, weight, size and the class (for example, graded in beginner, advanced runner, competitive athlete, etc.). Furthermore, health risk factors such as high blood pressure, heart diseases or nicotine consumption are preferably queried and drawn upon as further test person-specific parameters $P_x$. For individualization of the results, further personal data can be input, such as the name of the test person 6 or an identification number.

After this, the module 16 calculates or determines a test program using stored characteristic data. In particular, using the parameters $P_x$, the module 16 determines the initial speed and the temporal speed curve.

At the beginning of the test, the module 16 outputs a start notification to the test person 6 via the control panel 12 and starts the treadmill 3 with the predetermined initial seed. During the test course, the module 16 determines the time curve of the heart rate HF together with the associated running speed v. Furthermore, the module 16 determines the course distance s covered.

The heart rate HF recorded during an exemplary test course is shown in FIGS. 3A, B together with the running speed v and the course distance s covered, dependent on the test duration t. In these test variants, as in the conventional Conconi test, the running speed v is increased in stages in regular intervals of the course s by a regular speed step $\Delta v$, until the test person 6 can no longer keep up with the running speed v predetermined by the treadmill 3 and aborts the test course by pressing a key on the control panel 12. The module 16 displays the measured heart rate HF together with the associated running speed v and the course distance s covered.

For evaluation, the module 16 analyzes the heart rate HF as a function of the associated running speed v. The dependency of the heart rate HF on the running speed v associated with the test course according to FIG. 3A is shown by example in FIG. 3B. The module 16 analyzes the curve course shown in FIG. 3B with prevalent mathematical methods, for example, differential formation, linear or non-linear regression, iterative adaptation to a model function, etc., and thus determines the transition displayed in FIG. 3B by an arrow 17 between the linear curve of the heart rate HF in the aerobic low-power range 18 and the behavior of the heart rate HF deviating from this in the anaerobic high-power range 19. From this, the module 16 determines the transition heart rate $HF_0$ characteristic for the LBP and the associated transition running speed $v_0$. In the event that the blood pressure has been collected, the module 16 draws upon the curve of the blood pressure of the test person 6 as support in the determination of the LBP.

In an alternative test course shown in FIGS. 4A, B, the control unit 4 increases the running speed v linearly, meaning, in particular, continuously with the run time t. In FIG. 4A, the time curve of the running speed v, the course distance s covered and the measured heart rate HF are exemplarily shown again.

The dependency resulting from this of the measured heart rate on the running speed is (analogous to FIG. 3B) illustrated in FIG. 4B. In the manner specified in connection with FIGS. 3A, B, the module 16 determines the LBP with the associated transition heart rate $HF_0$ and the transition running speed $v_0$.

The measurement curve according to FIG. 3B or, respectively, FIG. 4B is preferably already displayed on the screen 15 of the control panel 12 during the test course or subsequently.

After the end of the test, the module 16 produces an individual training recommendation 20 for the test person 6 using the determined LBP, the collected test person-specific parameters $P_x$ and stored empirical characteristic data. The module 16 outputs these to the test person 6 via the printer 13. Such a training recommendation 20 is exemplarily shown in FIG. 5.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

REFERENCE LIST

| | |
|---|---|
| 1 | apparatus |
| 2 | motor |
| 3 | treadmill |
| 4 | control unit |
| 5a, 5b | pulse measurement device |
| 6 | test person |
| 7 | IR transmitter |
| 8 | light line |
| 9 | mount |
| 10 | IR receiver |
| 11 | handhold |
| 12 | control panel |
| 13 | printer |
| 14 | keypad |
| 15 | screen |
| 16 | module |
| 17 | arrow |
| 18 | low-power range |
| 19 | high-power range |
| 20 | training recommendation |
| v | running speed |
| HF | heart rate |
| $P_x$ | parameter |
| s | course distance |
| t | test duration |
| $\Delta v$ | speed step |
| $HF_0$ | transition heart rate |
| $V_0$ | transition running speed |

What is claimed is:

1. An apparatus for training adjustment in sports, comprising:
   a motorized treadmill for which a running speed can be predetermined;
   a pulse measurement device configured to supply a measurement value of the heart rate of a test person;
   a control unit connected to the pulse measurement device, the control unit configured to control the running speed of the motorized treadmill, the control unit comprising:
      a module to determine a lactate balance point, the module comprising:
         a mechanism to successively increase the running speed in a training course;
         a mechanism to register a time curve of the heart rate; and
         a mechanism to determine the lactate balance point of the test person via evaluation of a dependency of the heart rate on the running speed;
         wherein the module is configured to establish the lactate balance point via determination of a transition heart rate which, given representation of the heart rate as a function of the associated running speed, characterizes the transition between a linear low-power range and a high-power range deviating therefrom.

2. The apparatus according to claim 1, wherein the module is configured to increase the running speed in regular intervals of a course distance or the run time.

3. The apparatus according to claim 1, wherein the module is configured to increase the running speed in regular speed steps.

4. The apparatus according to claim 1, wherein the module is configured to vary the running speed as a continuously increasing function of the run time or of a course distance.

5. The apparatus according to claim 1, wherein at least one test person-specific parameter is associated with the module, and that the module is configured to determine a run time-dependent or a course distance-dependent curve of the running speed dependent on this parameter.

6. The apparatus according to claim 5, wherein the module is configured to utilize a characteristic selected from the group consisting of age, weight, height, class, and at least one health risk factor as a test person-specific parameters.

7. The apparatus according to claim 1, further comprising:
   an output unit connected with the module to output or display at least one of a measurement curve of the heart rate and the lactate balance point.

8. The apparatus according to claim 7, wherein the output unit is a screen.

9. The apparatus according to claim 7, wherein the output unit is a printer.

10. An apparatus for training adjustment in sports, comprising:
    a motorized treadmill for which a running speed can be predetermined;
    a pulse measurement device configured to supply a measurement value of the heart rate of a test person;

a control unit connected to the pulse measurement device, the control unit configured to control the running speed of the motorized treadmill, the control unit comprising:
   a module to determine a lactate balance point, the module comprising:
      a mechanism to successively increase the running speed in a training course;
      a mechanism to register a time curve of the heart rate; and
      a mechanism to determine the lactate balance point of the test person via evaluation of a dependency of the heart rate on the running speed;
the apparatus further comprising:
   a non-invasive blood-pressure measurement device connected to the module to provide a measurement value of the test person's blood pressure, the module further comprising a recording mechanism to record a curve of the blood pressure and to draw upon this for support to determine the lactate balance point.

11. The apparatus according to claim 5, wherein the module is configured to generate and output an individual training recommendation for the test person using the determined lactate balance point and the at least one test person-specific parameter.

* * * * *